US012211368B2

(12) United States Patent
Beyer et al.

(10) Patent No.: US 12,211,368 B2
(45) Date of Patent: *Jan. 28, 2025

(54) USER PREFERENCES IN RESPONDER NETWORK RESPONDER SELECTION

(71) Applicant: Avive Solutions, Inc., Brisbane, CA (US)

(72) Inventors: Rory M. Beyer, San Mateo, CA (US); Micah R. Bongberg, Kirkland, WA (US); Sameer Jafri, San Diego, CA (US)

(73) Assignee: Avive Solutions, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/521,405

(22) Filed: Nov. 28, 2023

(65) Prior Publication Data

US 2024/0096203 A1  Mar. 21, 2024

Related U.S. Application Data

(63) Continuation of application No. 17/501,900, filed on Oct. 14, 2021, now Pat. No. 11,869,338.

(60) Provisional application No. 63/093,568, filed on Oct. 19, 2020.

(51) Int. Cl.
*G08B 27/00* (2006.01)
*G08B 25/00* (2006.01)

(52) U.S. Cl.
CPC ......... *G08B 27/001* (2013.01); *G08B 25/003* (2013.01); *G08B 25/006* (2013.01); *G08B 25/009* (2013.01)

(58) Field of Classification Search
CPC ... G08B 27/001; G08B 25/003; G08B 25/006
See application file for complete search history.

(56) References Cited

U.S. PATENT DOCUMENTS

| 6,292,687 B1 | 9/2001 | Lowell et al. |
| 6,356,785 B1 | 3/2002 | Snyder et al. |
| 6,493,581 B2 | 12/2002 | Russell |

(Continued)

FOREIGN PATENT DOCUMENTS

| CN | 105013085 | 11/2015 |
| CN | 108671401 | 10/2018 |

(Continued)

OTHER PUBLICATIONS

Beyer et al., U.S. Appl. No. 17/501,900, filed Oct. 14, 2021.
Bongberg et al., U.S. Appl. No. 17/217,738, filed Mar. 30, 2021.

*Primary Examiner* — Andrew W Bee
(74) *Attorney, Agent, or Firm* — Beyer Law Group LLP

(57) ABSTRACT

Methods, user interfaces and systems are described that enable responder preferences to be considered during deployment of a public responder network. In some embodiments, a user is able to set preferences such as a mobility status, a public accessibility preference, a incidents notifications preference or a geographic preference associated with a medical device that is a part of the public responder network. In some embodiments, the user is able to select or define an area for which incident notifications are desired or are to be restricted in some manner. The described approach is well suited for public responder networks that include medical devices such as defibrillators (e.g., AEDs) in the network.

21 Claims, 8 Drawing Sheets

(56) References Cited

U.S. PATENT DOCUMENTS

| | | |
|---|---|---|
| 6,658,290 B1 | 12/2003 | Lin et al. |
| 6,747,556 B2 | 6/2004 | Medema et al. |
| 6,834,207 B2 | 12/2004 | Miyauchi et al. |
| 6,937,150 B2 | 8/2005 | Medema et al. |
| 6,993,386 B2 | 1/2006 | Lin et al. |
| 7,289,029 B2 | 10/2007 | Medema et al. |
| 8,086,320 B2 | 12/2011 | Saketkhou |
| 8,180,457 B2 | 5/2012 | Matos |
| 8,209,008 B2 | 6/2012 | Hansen et al. |
| 8,565,871 B2 | 10/2013 | Tuysserkani |
| 8,706,225 B2 | 4/2014 | Matos |
| 8,818,522 B2 | 8/2014 | Mass et al. |
| 8,880,168 B2 | 11/2014 | Pearce et al. |
| 8,981,927 B2 | 3/2015 | McSheffrey |
| 9,026,147 B2 | 5/2015 | Galvin et al. |
| 9,035,787 B2 | 5/2015 | Bongberg et al. |
| 9,101,527 B2 | 8/2015 | Madanat |
| 9,232,040 B2 | 1/2016 | Barash et al. |
| 9,289,621 B2 | 3/2016 | Aoyama et al. |
| 9,295,849 B2 | 3/2016 | Elghazzawi et al. |
| 9,307,383 B1 | 4/2016 | Patrick |
| 9,324,120 B2 | 4/2016 | Braun |
| 9,480,852 B2 | 11/2016 | Bonnamy |
| 9,498,152 B2 | 11/2016 | Bowers |
| 9,592,401 B2 | 3/2017 | Freeman et al. |
| 9,619,767 B2 | 4/2017 | Braun |
| 9,628,946 B2 | 4/2017 | Elghazzawi |
| 9,847,030 B2 | 12/2017 | Kadobayashi et al. |
| 9,848,058 B2 | 12/2017 | Johnson et al. |
| 9,872,998 B2 | 1/2018 | Aoyama et al. |
| 9,889,311 B2 | 2/2018 | Horseman et al. |
| 9,897,459 B2 | 2/2018 | Johnson |
| 9,987,193 B2 | 5/2018 | Freeman |
| 10,029,109 B2 | 7/2018 | Beyer et al. |
| 10,035,023 B2 | 7/2018 | Das |
| 10,058,469 B2 | 8/2018 | Freeman |
| 10,058,709 B2 | 8/2018 | Tilton, Jr. |
| 10,090,716 B2 | 10/2018 | Stever et al. |
| 10,092,767 B1 | 10/2018 | Newton et al. |
| 10,099,061 B2 | 10/2018 | Buchanan |
| 10,159,848 B2 | 12/2018 | Amann et al. |
| 10,178,534 B2 | 1/2019 | Barash et al. |
| 10,298,072 B2 | 5/2019 | Stever et al. |
| 10,381,118 B2 | 8/2019 | Kellum |
| 10,449,380 B2 | 10/2019 | Andrews |
| 10,504,622 B2 | 12/2019 | Gallopyn et al. |
| 10,543,379 B2 | 1/2020 | Hingston et al. |
| 10,565,845 B1 | 2/2020 | Beyer et al. |
| 10,580,280 B1 | 3/2020 | Picco et al. |
| 10,621,846 B1 | 4/2020 | Beyer et al. |
| 10,638,929 B2 | 5/2020 | Kaib et al. |
| 10,657,796 B2 | 5/2020 | Bowers |
| 10,665,078 B1 | 5/2020 | Picco et al. |
| 10,737,105 B2 | 8/2020 | Andrews et al. |
| 10,744,063 B2 | 8/2020 | Freeman |
| 10,773,091 B2 | 9/2020 | Andrews et al. |
| 10,792,506 B2 | 10/2020 | Elghazzawi |
| 10,796,396 B2 | 10/2020 | Braun et al. |
| 10,806,939 B1 | 10/2020 | Malott et al. |
| 10,857,371 B2 | 12/2020 | Gustavson et al. |
| 10,861,310 B2 | 12/2020 | Picco et al. |
| 10,946,209 B2 | 3/2021 | Andrews et al. |
| 10,957,178 B2 | 3/2021 | Beyer et al. |
| 11,077,312 B2 | 8/2021 | Sturman et al. |
| 11,138,855 B2 | 10/2021 | Jafri et al. |
| 11,645,899 B2 | 5/2023 | Jafri et al. |
| 2003/0028219 A1 | 2/2003 | Powers et al. |
| 2003/0149759 A1 | 8/2003 | Hetherington et al. |
| 2004/0015191 A1 | 1/2004 | Otman et al. |
| 2004/0049233 A1 | 3/2004 | Edwards |
| 2004/0064342 A1 | 4/2004 | Browne et al. |
| 2006/0030891 A1 | 2/2006 | Saltzstein et al. |
| 2006/0041278 A1 | 2/2006 | Cohen et al. |
| 2006/0149321 A1 | 7/2006 | Merry et al. |
| 2006/0149322 A1 | 7/2006 | Merry et al. |
| 2006/0149323 A1 | 7/2006 | Merry et al. |
| 2007/0032830 A1 | 2/2007 | Bowers |
| 2007/0136099 A1 | 6/2007 | Neligh et al. |
| 2007/0162075 A1 | 7/2007 | O'hara |
| 2007/0270909 A1 | 11/2007 | Saketkhou |
| 2007/0299473 A1 | 12/2007 | Matos |
| 2008/0250166 A1 | 10/2008 | Edwards |
| 2009/0070148 A1 | 3/2009 | Skocic |
| 2009/0149894 A1 | 6/2009 | Merry et al. |
| 2009/0284378 A1 | 11/2009 | Ferren et al. |
| 2010/0017471 A1 | 1/2010 | Brown et al. |
| 2010/0174560 A1 | 7/2010 | Quan et al. |
| 2010/0286490 A1 | 11/2010 | Koverzin |
| 2011/0060378 A1 | 3/2011 | Tuysserkani |
| 2011/0071880 A1 | 3/2011 | Spector |
| 2011/0117878 A1 | 5/2011 | Barash et al. |
| 2011/0152702 A1 | 6/2011 | Goto |
| 2012/0232355 A1 | 9/2012 | Freeman |
| 2013/0012151 A1 | 1/2013 | Hankins |
| 2013/0065628 A1 | 3/2013 | Pfeffer |
| 2013/0296719 A1 | 11/2013 | Packer et al. |
| 2014/0002241 A1 | 1/2014 | Elghazzawi |
| 2014/0004814 A1 | 1/2014 | Elghazzawi |
| 2014/0031884 A1 | 1/2014 | Elghazzawi |
| 2014/0222096 A1 | 8/2014 | Hu et al. |
| 2014/0222466 A1 | 8/2014 | Kellum |
| 2015/0206408 A1 | 7/2015 | LaLonde et al. |
| 2015/0343229 A1 | 12/2015 | Peterson et al. |
| 2016/0066653 A1 | 3/2016 | Piva et al. |
| 2016/0133160 A1 | 5/2016 | Packer et al. |
| 2016/0140834 A1 | 5/2016 | Tran |
| 2016/0148495 A1 | 5/2016 | Buchanan |
| 2016/0210581 A1 | 7/2016 | Braun |
| 2016/0213942 A1 | 7/2016 | Elghazzawi et al. |
| 2016/0328950 A1 | 11/2016 | Pelletier et al. |
| 2017/0021185 A1 | 1/2017 | Das |
| 2017/0028211 A1 | 2/2017 | Tilton, Jr. |
| 2017/0172424 A1 | 6/2017 | Eggers et al. |
| 2017/0251347 A1 | 8/2017 | Mehta et al. |
| 2017/0273116 A1 | 9/2017 | Elghazzawi |
| 2017/0281016 A1 | 10/2017 | Elghazzawi |
| 2017/0281461 A1 | 10/2017 | Kokubo et al. |
| 2017/0289350 A1 | 10/2017 | Philbin |
| 2017/0367927 A1 | 12/2017 | Cervantes |
| 2018/0169426 A1 | 6/2018 | Montague et al. |
| 2018/0369598 A1 | 12/2018 | Newton et al. |
| 2019/0038133 A1 | 2/2019 | Tran |
| 2019/0044362 A1 | 2/2019 | Beyer et al. |
| 2019/0099608 A1 | 4/2019 | Elghazzawi et al. |
| 2019/0117983 A1 | 4/2019 | Andrews et al. |
| 2019/0117984 A1 | 4/2019 | Andrews et al. |
| 2019/0117987 A1 | 4/2019 | Beyer et al. |
| 2019/0117988 A1 | 4/2019 | Beyer et al. |
| 2019/0124466 A1 | 4/2019 | Masterson et al. |
| 2019/0159009 A1 | 5/2019 | Barash et al. |
| 2019/0168010 A1 | 6/2019 | Elghazzawi |
| 2019/0174289 A1 | 6/2019 | Martin et al. |
| 2019/0279327 A1 | 9/2019 | Braun et al. |
| 2019/0306664 A1 | 10/2019 | Mehta et al. |
| 2019/0318827 A1 | 10/2019 | Chiu et al. |
| 2020/0054885 A1 | 2/2020 | Aprile |
| 2020/0090483 A1 | 3/2020 | Picco et al. |
| 2020/0092700 A1 | 3/2020 | Picco et al. |
| 2020/0206517 A1 | 7/2020 | Martin et al. |
| 2020/0221263 A1 | 7/2020 | Sturman et al. |
| 2020/0242907 A1 | 7/2020 | Beyer et al. |
| 2020/0286352 A1 | 9/2020 | Beyer et al. |
| 2020/0286353 A1 | 9/2020 | Jafri et al. |
| 2020/0373005 A1 | 11/2020 | Halsne et al. |
| 2021/0136531 A1 | 5/2021 | Dorian et al. |
| 2021/0142639 A1 | 5/2021 | Beyer et al. |
| 2021/0153817 A1 | 5/2021 | Beyer et al. |
| 2021/0154487 A1 | 5/2021 | Bongberg et al. |
| 2021/0228893 A1 | 7/2021 | Akram |
| 2021/0314757 A1 | 10/2021 | Pellegrini et al. |

(56) References Cited

U.S. PATENT DOCUMENTS

FOREIGN PATENT DOCUMENTS

| | | |
|---|---|---|
| CN | 111539866 | 8/2020 |
| DE | 202004002106 | 6/2004 |
| EP | 1157717 | 1/2005 |
| EP | 2218478 | 8/2010 |
| EP | 2879759 | 10/2019 |
| JP | 2001/325689 | 11/2001 |
| KR | 20160012239 | 2/2016 |
| KR | 101780214 | 10/2017 |
| KR | 102152282 | 9/2020 |
| WO | 2010/66014 | 6/2010 |
| WO | 2018/069383 | 4/2018 |

Location Status

| AEDs | Battery | Pad Cartridge | Other Issues | Sync Status |
|---|---|---|---|---|
| 4 | ● Good 19<br>⊙ Low 1<br>Unknown 0 | ● Good 18<br>⊙ Replace 1<br>⊙ Re-Install 1<br>○ Upcoming 1<br>Unknown 0 | ⊙ Critical Test 1<br>⊙ Training 1<br>○ Software 1<br>○ Temp. 1<br>Unknown 0 | ● Synced 20<br>Unsynced 0 |

AED Assignments 365

FILTER [Health ▼] [Labels ▼] [Search ▼]

GPS Last Updated (xxxxxx @xxxx) [REFESH GPS]

| AED Name | Health |
|---|---|
| C34309 | ● |
| C34310 | ⊙ Battery low, Training pads inserted |
| C34311 | ⊙ Battery low |
| C34312 | ○ Pads expiring soon |

393, 394, 396, 397

Rows per page [4 ▼] 1 of 1 |< < > >|

Location Info
Name of Location
Law Office San Francisco

Adress:
223 Mississippi Street
Unit 2
San Francisco, CA 94901

Location Labels
Headquarters

Location Accessibility
Private of Public
Public

Accessibility
Sunday: Not Available
Monday-Friday: 9AM-6PM
Saturday: 11AM-10PM          380

GEO Fence AED [ON]
AED will only respond to emergencies within determined boundary.

Store   VIEW FULL STORE

| AED | 0 |
|---|---|
| Electrode Pads | 2 |
| Training Pads | 2 |

[ORDER]

User Assignments # of Users: 8
CPR Certified: Uncertified 7:1

FILTER [User Name ▼] [User Role ▼] [Labels ▼]

| User Name | User Role | Labels | |
|---|---|---|---|
| Abdul Price (Primary Contact) | Admin | Nurse | ☆CPR Certified |
| Sierra Avila | Admin | | ☆CPR Certified |
| Faye Redman | Manager | Nurse | ☆CPR Certified |
| Manveer Parks | Manager | | ☆CPR Certified |
| Dilen Goulding | Responder | | ☆CPR Certified |

Documents

*FIG. 6*

USER PREFERENCES IN RESPONDER NETWORK RESPONDER SELECTION

CROSS-REFERENCE TO RELATED APPLICATIONS

This application is a Continuation of U.S. application Ser. No. 17/501,900, filed on Oct. 14, 2021, which claims priority of U.S. Provisional Application No. 63/093,568, filed on Oct. 19, 2020, both of which are incorporated by reference herein in their entirety.

FIELD

The present disclosure relates generally to public responder networks.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed so that they can be used by a lay person in situations where professional medical help is not available.

Given their potential to save lives, automated external defibrillators have been deployed in a relatively wide variety of public and private locations so that they are available in the event that a person in the vicinity goes into cardiac arrest. By way of example, AEDs may be found in corporate and government offices, shopping centers, airports, airplanes, restaurants, casinos, hotels, sports stadiums, schools, fitness centers and a variety of other locations where people may congregate.

Although AEDs have been deployed in a number of locations, AEDs are not always immediately available when a cardiac arrest incident occurs. To help address this issue, there have been several efforts to develop public responder networks through which volunteer responders and/or AEDs are notified of nearby cardiac arrest incidents and citizen responders are encouraged to take an AED to the incident scene. Although existing volunteer responder networks have had positive impacts on cardiac arrest survival rates, there are continuing efforts to develop techniques and approaches that improve the effectiveness of volunteer responder networks.

U.S. Pat. No. 10,580,280 (P014B); U.S. Pat. No. 10,565,845 (P014A); U.S. Pat. No. 10,957,178 (P014X1); U.S. Pat. No. 11,138,855 (P014AX2); U.S. Pat. No. 11,645,899 (P014X3); and U.S. patent application Ser. No. 17/100,154 (P020A); Ser. No. 17/100,313 (P020B) and 63/242,610 (P025P) describe responder networks designed to send incident alerts to connected AEDs and/or volunteer responders when a potential cardiac arrest incident occurs nearby. Each of these patents/patent applications are incorporated herein by reference. When an AED receives an incident alert, it may generate an audio and/or visual alert designed to attract the attention of people nearby and encourage them to take the AED to the scene of the incident. The "people nearby" may be a person or persons connected with the AED (e.g., the AED's owner or administrator, an office in which the AED is located, etc.) or simply a bystander that happens to be nearby when the alert is generated. Similarly, nearby citizen volunteers may be encouraged to take an AED to the incident. In the context of this application, both volunteer citizen responders and notified AEDs are both sometimes referred to as "responders" herein for simplicity.

One challenge that occurs in designing a responder network is identifying which responders to notify of a nearby incident. Some responder networks notify all responders that are located within a defined radius of an incident. Others have proposed having a public safety answering point (PSAP) operator select one or more specific responder. Although both of these types of approaches can work well, they each have drawbacks as well. Therefore, there are continuing efforts to develop improved responder selection criteria. U.S. Provisional Patent Application Nos. 62/834,137 (P017P) and 62/928,329 (P017P2), which are incorporated herein by reference, describes approaches for weighing a number of factors in the determination of which responders to identify.

The present application describes additional factors that may be utilized in the selection of which potential responders to notify of a nearby incident.

SUMMARY

A variety of methods, user interfaces and responder network systems are described that enable responder preferences to be considered during deployment of a public responder network. In one aspect a user or administrator is able to set preferences regarding how or whether a medical device, such as a defibrillator, is incorporated into a volunteer/public responder network. Such preferences may include characteristics such as a device mobility setting, a device accessibility setting, an incident notification setting, geographic preferences, etc.

In some embodiments, available device mobility settings include: a stationary setting that indicates that an associated medical device (e.g., defibrillator) is expected to be kept at a fixed location; and a mobile setting that indicates that the medical device is expected to be moved around.

In some embodiments, available public accessibility settings include: a public setting that indicates that the medical device is available to the public; and a private setting that indicates that the medical device is not available to the public.

In some embodiments, the available incident notifications settings include: an incident notifications enabled setting that indicates that notifications of nearby emergency incidents are authorized to be sent to the medical device; and an incident notifications not enabled setting that indicates that notifications of nearby potential cardiac arrest incidents are not authorized to be sent to the first defibrillator.

In some embodiments, the available geographic preferences include an always notify option, wherein when the always notify option is selected, a selection algorithm will cause the medical device to be notified any time a request to activate the public responder network is received for a relevant incident occurring within a designated area associated with the medical device. The available geographic preferences may also include an available option, wherein when the available option is selected and a relevant incident occurs within the designated area, the selection algorithm may optionally include the medical device in a set of devices to be notified based on other factors.

In some embodiments, the medical device is a defibrillator such as an automated external defibrillator (AED).

In another aspect, a user is able to select or define an area for which medical incident notifications are desired. In some embodiments, the associated device/responder will not be notified of any incidents that occur outside of the designated area as part of the responder network response. In some embodiments the device that is excluded from the response is a medical device, such as a defibrillator—e.g., an automated external defibrillator (AED).

In some implementations, the associated responder/device will always be notified of incidents occurring within the defined area, whereas in other implementations, the associated responder/device is treated as a candidate that a responder selection algorithm may optionally select, or not select, for notification based on other criteria. In some embodiments, the user is given control over which of these approaches is used.

In some embodiments, the responder network is configured to send incident notifications to a designated set of responders and/or devices and/or stations when an incident occurs within the designated area.

In another aspect, a graphical user interface provides a mechanism for setting user preferences associated with the medical device's participation in a medical device inclusive volunteer responder network. Each medical device in the volunteer responder network is configured to generate a nearby incident alert in response to the reception of a nearby incident notification to encourage individuals that perceive the nearby incident alert to take such medical device to a nearby emergency incident. In various embodiments, the graphical user interface includes one or more: (i) a mobility status selector for designating a mobility status of the medical device; (ii) a public accessibility selector for designating a public accessibility of the medical device; (iii) an incident notifications selector for designating whether nearby incident alerts are permitted for the medical device; and (iv) a geographic preference selection mechanism for designating a geographic preference associated with the medical device.

BRIEF DESCRIPTION OF THE DRAWINGS

The invention and the advantages thereof, may best be understood by reference to the following description taken in conjunction with the accompanying drawings in which:

FIG. 6 is a screen shot of the user interface of FIG. 5 with a geo-fencing tool enabled to permit the user to define an area for which notifications should not be sent to outside devices/responders.

In the drawings, like reference numerals are sometimes used to designate like structural elements. It should also be appreciated that the depictions in the figures are diagrammatic and not to scale.

DETAILED DESCRIPTION OF THE DRAWINGS

The present disclosure relates generally to public responder networks—as for example, a network of defibrillators (e.g., AEDs) available for use during a potential cardiac arrest incident and/or a network of volunteer responders willing to respond to such an event. A variety of methods, devices, user interfaces and software applications are described that enable user/responder/administrator preferences to be considered when determining what devices/potential responders to notify of a particular emergency incident. The inventions are described primarily in the context of a network of defibrillators (e.g., AEDs) and volunteers willing to respond to cardiac arrest incidents. However, it should be appreciated that similar approaches and systems can be used in conjunction with responder networks involving other types of incidents, treatments and/or devices.

The Applicant is developing automated external defibrillator systems that include a number of connectivity features and/or are well suited for use in AED inclusive public responder networks. By way of example, U.S. Pat. No. 10,773,091 (P006E); U.S. Pat. No. 10,737,105 (P006A); U.S. Pat. No. 11,077,312 (P016B), and U.S. Pat. No. 10,029,109 (P001A) (each of which is incorporated herein by reference) describe a few such devices.

Figure 1A:
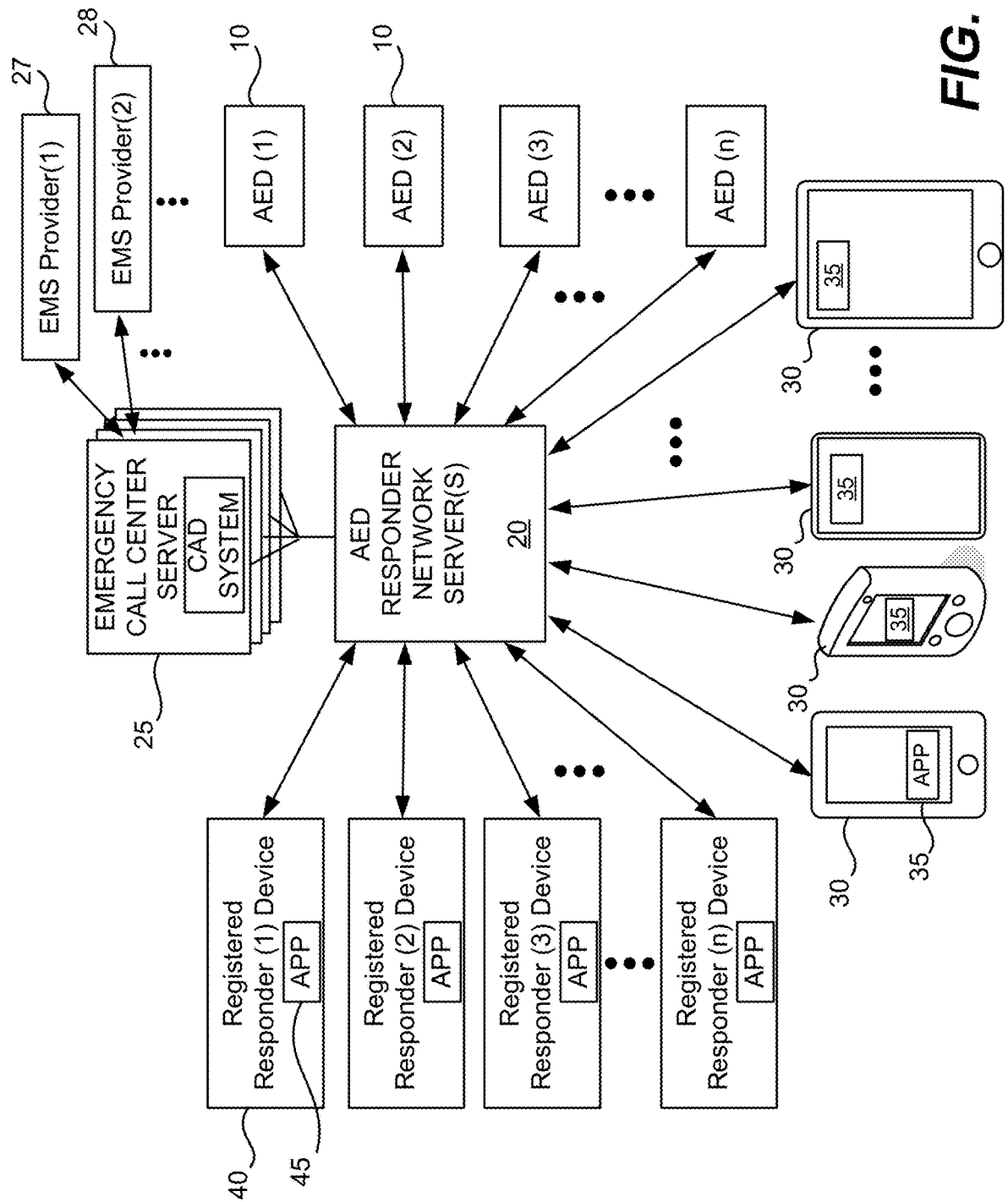
FIG. 1A is a schematic diagram illustrating components of a public responder network for notifying potential responders of nearby potential cardiac arrest incidents.
Figure 1B:
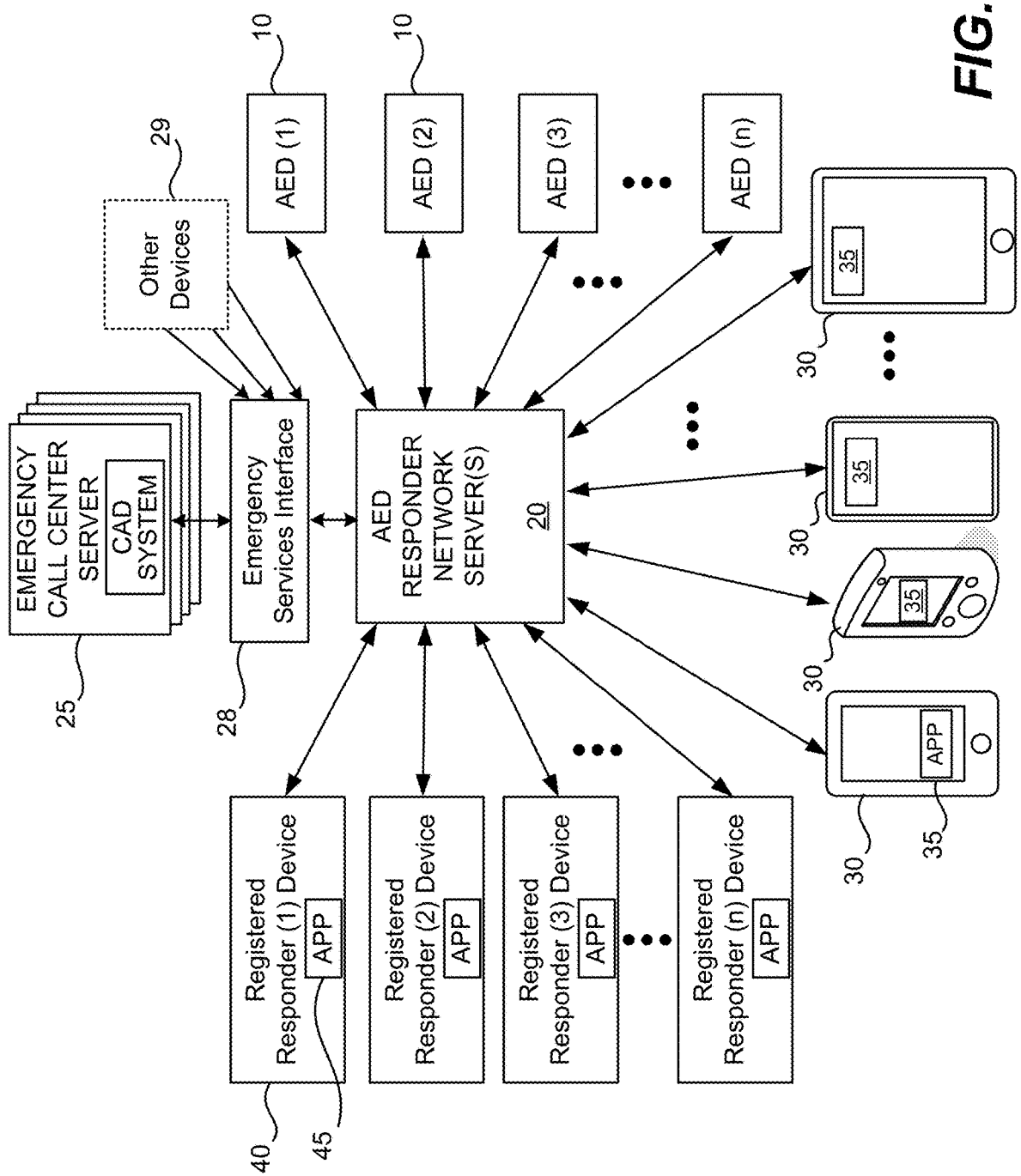
FIG. 1B is a schematic diagram illustrating components of an alternative public responder network for notifying potential responders of nearby potential cardiac arrest incidents that utilizes an emergency services interface.

Components of a public, AED inclusive responder network of the type contemplated herein are diagrammatically illustrated in FIGS. 1A and 1B. In the embodiment illustrated in FIG. 1A, the network includes a number of AEDs 10 that have connectivity features which facilitate communications with one or more servers—which is/are referred to in FIG. 1A as AED response network server(s) 20. Some of the AEDs described in the incorporated patents and patent applications work well for this purpose, but the network is not in any way limited to such AEDs. In some embodiments, some of the AEDs 10 may be modular defibrillator systems that include a fully functional base defibrillator and an interface unit that is mounted on and detachably attached to the base defibrillator unit to provide a unitary portable modular defibrillator. In such embodiments, the interface unit may include components such as a display screen and a communication unit suitable for communicating with the AED response network server through an appropriate communications network. The incorporated U.S. Pat. No. 10,773,091 (P006E); U.S. Pat. No. 10,737,105 (P006A); and U.S. Pat. No. 11,077,312 (P016B) describe some such systems. In other embodiments, the communications capabilities may be provided in a variety of different ways. For example, the communications module may be incorporated into a unitary defibrillator housing, or in a modular system, into the base defibrillator unit. Alternatively, the communications unit may be a unit that plugs into a defibrillator or takes any other suitable form.

The AED response network server(s) 20 is arranged to communicate directly or indirectly with existing emergency response networks and systems, including, for example, computer aided dispatch (CAD) systems commonly used by emergency call/dispatch centers. These are sometimes collectively referred to as emergency services servers (25) and a particular class of emergency services servers referred to as emergency call center servers(s) is illustrated in FIG. 1A. Emergency call centers are Public Safety Answering Points (PSAPs) such as 911 call centers in the U.S. and Canada, 112 call centers in Europe, 999 call centers in some jurisdictions and other such emergency services call centers.

The emergency call/dispatch centers 25 are typically able to communicate separately with a variety of emergency medical service providers (EMS providers) 27 which may include emergency medical technicians, ambulance services, fire department personnel, etc.

In various embodiments, the AED response network server can be hosted by an advocacy group or a private party such as a defibrillator manufacturer or an entity that manages a large number of AEDs. Alternatively, the functionality of AED response network server(s) 20 could be incorporated into a server (or servers) within an emergency services interface (discussed below). In other embodiments, the functionality of the AED response server(s) 20 can be incorporated into other components of public safety and/or emergency response networks.

The network may also include a number of user devices 30 each having a user app 35 or other suitable software installed thereon that is configured to communicate with one or more of the AEDs, and with the AED response network server 20. The AED user devices 30 are frequently (but not necessarily) devices associated with the AED's owners, administrators and/or other responsible parties. The AED user devices 30 may take a wide variety of different forms including mobile phones, tablet computers, as well as other types of personal communication and/or computing devices. The network also has a number of volunteer responders who have registered to indicate their desire to receive notification of nearby emergency incidents for which assistance may be helpful. In the context of a responder network focused on sudden cardiac arrest, the volunteer responders would presumably and preferably be trained in CPR and the use of an AED.

The volunteer responders have their own user devices 40 (e.g., smart phones, tablets, smart watches, or other computing or mobile/personal communication devices) which have a responder app 45 or other suitable software installed thereon with which they can communicate and receive communications from the AED response network server 20. Like the AED user devices 30 and user app 35, the responder user devices 40 and responder app 45 may take a wide variety of different forms (e.g., smart phones, tablets, smart watches or other computing or mobile/personal communication devices) and they are labeled differently in the drawings merely to highlight the different context that the devices and app are used for. In some embodiments, a single app may be used as both apps 35 and 45 with the primary difference being whether the user has registered as a volunteer responder or as an AED administrator/owner, and the functionality of the app that may be accessed after such registration. Of course, in other embodiments separate apps may be provided. It should be appreciated that there is no need for all of the apps to be the same and/or to come from one source. Rather, the emergency response functionality can be incorporated into a wide variety of different applications or software components provided by different entities, including defibrillator manufacturers, health service providers, advocacy groups, emergency service providers, user device manufacturers, health applications (e.g., the Apple Health app.), neighborhood watch apps (e.g., the Ring Neighbors app); etc.

In some specific implementations, the user app may be embodied in the form of an AED app that is designed to be capable of use in conjunction with selected defibrillators during the event of an emergency to help guide a lay responder through the use of the AED and/or to help facilitate the transmission of incident information to emergency responders and other concerned medical personnel. Thus, for convenience, in much of the discussion below, the app is referred to as an AED app. However, it should be appreciated that the user application software may take a very wide variety of forms and is not intended to be limited to apps having AED support functionalities.

The AED response network server(s) 20 can also take a wide variety of different forms and are generally intended to refer to any central systems or combinations of systems configured to execute the necessary functionality of the server. By way of example the AED response network server may take the form of one or more computing devices, server clusters, distributed computing nodes on a network or the combined forces of multiple distinct systems. Such servers can be operated by public or private entities of any nature including emergency services, non-profit advocacy organizations, healthcare organizations, medical device companies, government agencies and/or any other suitable entities. The AED response network servers can be dedicated to handling AED response network actions, they can be integrated into AED management server platforms, they can be integrated into components of existing emergency services networks, and/or they can be deployed as part of a variety of other now existing or later developed systems.

FIG. 1B illustrates another representative responder network architecture. This embodiment is quite similar to the embodiment discussed above with respect to FIG. 1A except that an emergency response network interface or an emergency services interface 28 serves as an interface between the AED response network server 20 and the emergency call centers 25. In the United States, RapidSOS is currently the largest emergency response network interface and is well suited for such applications. One particularly desirable feature of RapidSOS is that they currently have relationships with a large percentage of the emergency call centers in the United States and are already set up to send incident related data received from other connected devices 29 to various call centers—although they do not currently serve as an intermediary between call centers and any defibrillators or defibrillator networks. Although RapidSOS is mentioned specifically, it should be appreciated that the same approach can be used with any or with multiple different intermediaries as appropriate.

Figure 2:
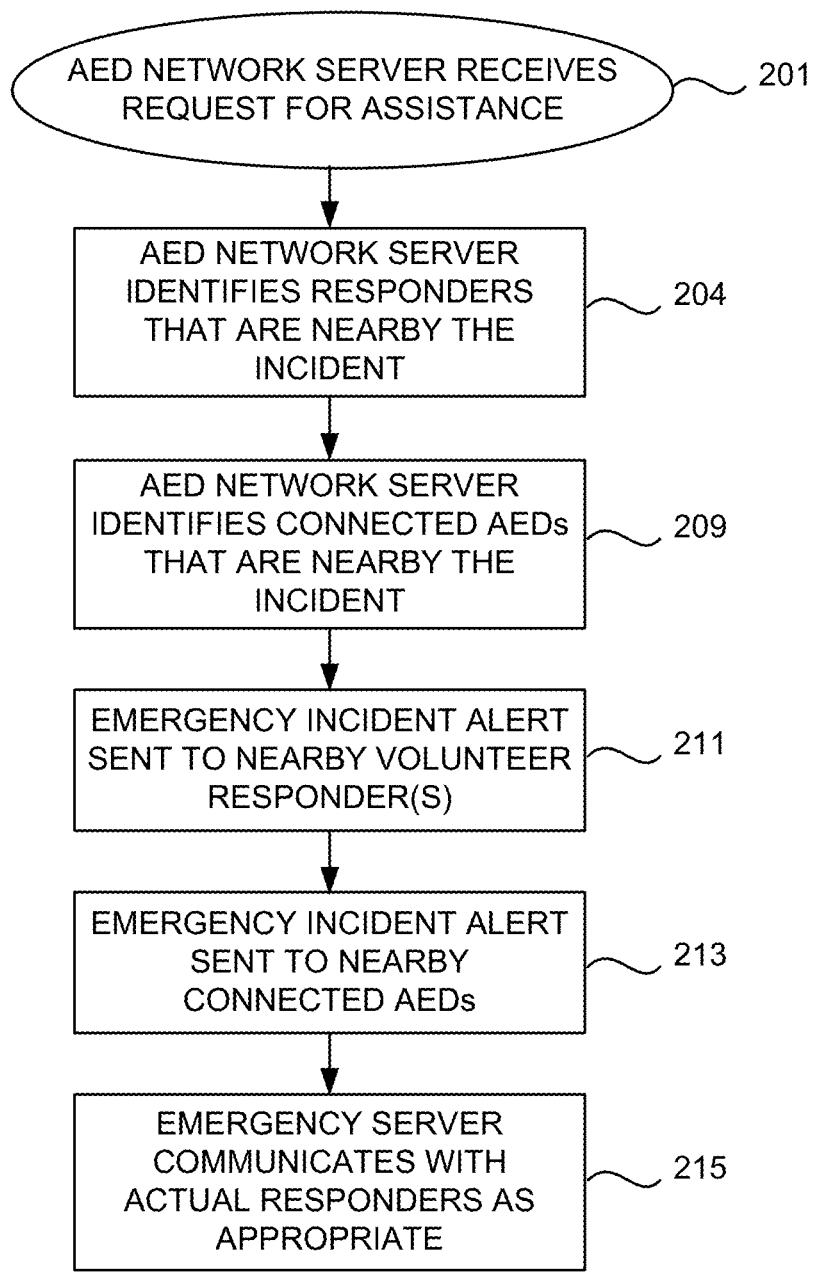
FIG. 2 is a flow chart illustrating a flow suitable for generating an incident alert to nearby AEDs and volunteer responders in response to a request for public AED assistance.

When a cardiac arrest incident occurs, the AED response network server 20 may receive a request for assistance. The request for assistance can come from a variety of different sources, including from an emergency services server 25 (directly or indirectly through an emergency services interface), a user app 35, from virtual assistants, from devices capable of detecting sudden cardiac arrest incidents or from any other suitable system. FIG. 2 is a flow chart illustrating a flow suitable for conveying alerts to nearby public AEDs and public responders in the event of a potential cardiac arrest incident in accordance with one embodiment.

When a request for assistance is received (step 201), the AED response network server 20 attempts to identify and select one or more registered volunteer responders and/or volunteer responder devices that are nearby the incident (step 204). The AED response network server also attempts to identify and select one or more known connected AEDs that are nearby the incident (step 209). The protocols, processes and algorithms used to identify suitable volunteers and AEDs may vary widely and a few suitable approaches are described in U.S. Pat. No. 10,565,845 (P014A); U.S. Pat. No. 10,621,846 (P014C1); U.S. Pat. No. 10,957,178 (P014X1); U.S. Pat. No. 11,645,899 (P014X3), and U.S. Pat. No. 11,138,855 (P014X2) and U.S. Patent Application Nos. 62/834,137 (P017P) and 62/928,329 (P017P2), each of which is incorporated herein by reference.

The AED response network server then sends a nearby incident notification to the selected registered volunteer responder(s)/devices that are close to the incident (step 211). The notification may be sent via any of a variety of different messaging technologies, including Apple IOS and Android push notification services, SMS text messages, other text or voice messaging protocols, multimedia messaging protocols (e.g., MMS), instant messaging or iMessage technologies, e-mail, etc. If a volunteer responder is nearby that either (a) has an AED or (b) can readily access an AED, then they can grab an AED and quickly bring the AED to the scene of the incident. In many situations, such a volunteer responder who may have an AED, or may know the location of a nearby AED, may be able to bring an AED to the scene quicker than a bystander to the incident trying to locate and fetch an AED or the time it takes EMS to arrive. The emergency incident nearby alert may be sent to any devices associated with the volunteer responder(s) that have been designated to receive such messages. Often this will be a Smartphone or similar mobile communication device. However, messages may be sent to any of a number of other types of devices in addition to, or in place of, a Smartphone, as for example, a tablet computer, a PDA, a smart watch, a smart speaker, a virtual assistant, a security system (e.g., a home, office, neighborhood or community security system), etc.

It should be appreciated that volunteer responder devices are not limited to devices associated with a specific individual. For example, the security guard station of a hotel, business, country club or living community may have a connected device that is registered to receive incident notification pertinent to their establishment or community. In another example, a home security network may be registered to receive incident notifications. Of course, there are many other examples as well.

In parallel with the notification of any nearby volunteer responders, nearby incident notifications may also be sent directly to any connected AEDs 10 that are close to the incident (step 213). As explained in some of the incorporated patents, the notified AED can issue a nearby incident alert signal meant to attract the attention of personnel or bystanders nearby the AED of the incident and request that they bring the AED to the incident location. Typically, such messages would only be sent to connected AEDs that have opted into the AED responder network.

In some embodiments, at least some of the AEDs 10 can be queried to report their current functionality status and current location. When such capabilities exist, each, or some of the AEDs that are believed to be nearby the incident can be queried (pinged) to provide its current status/location as part of AED identification step 209. Each of pinged AEDs then responds giving its current status and location information and that current information can be used to help determine which AEDs to send an emergency incident alert to in step 213. A few approaches for selecting a subset of AEDs to notify out of a larger responding set of AEDs are described in the incorporated U.S. Pat. No. 10,565,845 (P14A); U.S. Pat. No. 10,621,846 (P014C1); U.S. Pat. No. 10,957,178 (P014X1); U.S. Pat. No. 11,645,899 (P014X3), and U.S. Pat. No. 11,138,855 (P014X2) and U.S. Patent Application Nos. 62/834,137 (P017P) and 62/928,329 (P017P2).

After nearby incident notifications have been sent to any nearby registered volunteer responders and/or registered connected AEDs, the AED response network server can communicate with any responder(s) that agree to respond to the incident as appropriate to help guide them to the location of the incident and convey other information that may be helpful in responding to the incident (step 215).

It should be appreciated that there are a number of scenarios in which causing the AED to issue a nearby incident alert may result in a defibrillator and possibly even a trained responder arriving at the site of a cardiac arrest incident faster than would otherwise occur. For example, in many circumstances a defibrillator may be positioned at a location that is near a designated responder—as for example, in the context of a school setting, the defibrillator may be positioned near (or in) the office of a coach, administrator, nurse or teacher that is a trained responder. In the context of an office building, the defibrillator may be positioned near an owner, administrator or other employee that is a trained responder. When the AED issues an alert, the alert may be heard by the trained responder. In such circumstances there is significant value to notifying the potential responder(s) of an emergency incident that may require a defibrillator in real time so that they can go to the scene and provide assistance as needed. Even when a designated responder (or registered volunteer responders) is not immediately available, there may be other responsible personnel near the location of a defibrillator and the alert generated by the AED will notify such personnel of the occurrence of a cardiac event in their vicinity that they may be able to help respond to. Again, using the context of a school setting, administrators, teachers, coaches or other responsible personnel that happen to be near the defibrillator at the time an incident can be encouraged to quickly take the defibrillator to the location of the incident. Still further, there is even value to informing bystanders (e.g., fans at a sporting event, students or visitor in the school, bystanders in a public space, etc.) that a defibrillator is needed at a nearby emergency incident since it is possible that such a bystander will be motivated to take the AED to the location of the emergency. Although the examples above focus somewhat on the context of a school, it should be appreciated that the same motivations apply in a wide variety of different scenarios.

As previously discussed, when the AED response network server 20 receives a request for assistance (e.g., step 201 of FIG. 2) or otherwise determines that a volunteer responder may be useful in a particular situation, the server will try to identify nearby AEDs and/or nearby volunteer responders (e.g., steps 204 and 209 of FIG. 2). There are a wide variety of selection protocols that may be used to identify potential AEDs and responders.

As discussed above, some connected AEDs have the ability to report their current status and current location. The location can be identified based on any of a wide variety of location services that may be available to pinpoint the location of the AED including: Global Navigation Satellite System (GNSS) (e.g., GPS) chips within the AED or an interface unit attached to the AED; cellular or Wi-Fi locating technologies; metropolitan beacon systems; etc. In such embodiments, the AED response network server can ping each, or some, of the connected AEDs that are believed to be within a designated distance or response time of the patient. As suggested above, the designated distance may be within a defined radius from the incident (e.g. a relatively large radius), or may be based on more sophisticated measures such as whether the device is identified as a static device that is expected to normally be kept in the same place, or a mobile device that may be expected to be moved around (e.g., placed in a vehicle or carried around by its owner). Alternatively, when available, estimated response times can be used.

The queried AEDs each communicate their functionality status and location to the AED response network server to inform the server as to whether they are in adequate operating condition to be utilized on a patient, otherwise defined as "functional AEDs." Once AED response network server 20 identifies the functional AEDs within a defined distance of the patient, the server 20 sends an emergency alert (step 213) to any such AEDs deemed appropriate. It is important to note that if any of the AEDs communicate with the AED response network server that they are not in adequate operating condition, otherwise defined as "non-functional AEDs", the server may eliminate these AEDs from consideration and not send these AEDs a nearby incident notification. The notification that a "functional AED" receives activates an audible and/or visual signal on the identified AEDs (sometimes referred to as a "Nearby Incident Alert") signifying that there is an emergency situation for which bystander assistance would be helpful. If a bystander notices the alert, they can "accept" the emergency indicating a willingness to bring the AED to the scene, a map and/or directions is/are displayed on the AED that the responder can use to navigate to the patient's location. Additionally, or alternatively, audible directions may be provided to the user.

Somewhat similarly, if a volunteer responder accepts an emergency, a suitable map and/or directions may appear on the volunteer's responder device 40 (e.g., Smartphone) and guide the volunteer responder as appropriate. In other circumstances the destination (e.g., a destination address or other identifying information) may be additionally or alternatively provided so that the volunteer responder may enter the destination in their own directions app as desired.) It should be appreciated that there may be several communications back and forth between the AED response network server 20 and the volunteer responder as appropriate. For example, the responder may be asked whether they have immediate access to an AED. If so, a map may be displayed on the responder device to guide the volunteer directly to the incident. If not, the map may display the location(s) of available AEDs and guide the volunteer to a functional AED that is the closest to being on the way to the incident and then to the incident itself so that the volunteer can bring the AED.

When desired, the AED response network server can also intelligently direct volunteer responders in a coordinated manner. For example, if a volunteer that saw a nearby incident alert on an AED has affirmatively indicated that they are responding to the incident by bringing the AED, a registered volunteer responder who is closer to the incident but doesn't have an AED in hand may be directed to proceed directly to the incident rather than diverting out of their way to find an available public AED. Of course, the specific protocols and priorities utilized in directing multiple volunteer responders can vary widely based on the priorities and design goals of the responder network management. This can include decisions regarding: how many volunteers and/or AEDs to send incident notifications to; when to call off additional potential responder(s) in the event that one or more other responders have affirmatively indicated that they are responding to the incident; when to terminate further broadcasts of an incident alert (e.g. due to professional emergency medical personnel arriving on the scene, or due to responses by other); how many AEDs to try to bring to an incident; whether and in what circumstances volunteer responders may be directed to travel directly to an incident even if they don't have an AED in hand; etc.

It is believed that many citizens will be more inclined to sign-up to be a responder and/or to have their AED receive notifications of nearby incidents if they have more control over the location and/or type(s) of incidents that they are notified of. That may be due to a reluctance to respond to incidents in which they likely don't know or have a connection with the victim, for business reason, or for a variety of other personal reasons. For example, a property or building management team may wish to receive notification of any incidents within the building(s), premise(s) or campus that they are responsible for, but not incidents that occur outside of that area. A security service for a gated community may only wish to receive alerts for emergencies that occur within their community. A homeowner with an AED may wish to receive notifications of incidents on their block or street or within their immediate neighborhood, but not incidents that are further away even though they may otherwise be within the responder network's normal/default notification radius. A friend or family member of a person that is particularly at risk may only want to be notified of an incident that occurs at the at-risk person's residence. Of course, there are many other examples, and the desires and motivations of different responders can vary dramatically.

Geo-Fencing

One way to give potential responders more control over the types of incidents that they wish to respond to is to utilize concepts analogous to geo-fencing. In general, a potential responder may define one or more geographic areas for which they would like to (or are willing to) receive notifications of incidents that occur within the designated area. The geographic area(s) of interest may be defined in any way desired by the potential responder. It can be confined to one or more specific addresses, a cluster of houses, a city block, a building complex, a campus or any other boundaries as defined by the AED administrator/potential responder.

To facilitate geo-fenced responder notifications, an AED configuration application, a responder sign-up application or other suitable applications (herein more generally referred to as the response profile configuration interface) may include a user interface that allows the AED administrator/responder to define geographic boundaries of the incidents that they would like to be notified of. As suggested above, the defined regions may be as small as a single household or as large as a community. Preferably, the potential responder is not required to limit their availability to any specific geographic region. Rather, the geo-fencing is provided as an option for those responders who would like to provide geographic constraints on incidents that they may be notified of.

On the server side, a responder dispatch system has a responder selection algorithm. The responder selection algorithm is designed to identify specific AEDs and/or specific volunteer responders to send incident alerts to. When a responder has not identified any geographic constraints, the responder selection algorithm determines whether to notify a particular responder based on other criteria which may include standard proximity factors. Alternatively, when the responder has identified geographic constraints, those constraints will be considered by the selection algorithm. For example, if a particular responder has indicated that they are only interested in receiving alerts/notifications for incidents within a particular area, that responder may be eliminated from consideration for incidents that occur outside of that area. Conversely, if an incident occurs inside the geographic area identified by the responder, the selection algorithm may increase the priority of notifying that responder of the incident. For example, in some implementations, the responder may be notified of any/all incidents within their stated geographic preference area(s). In other implementations, a calculated selection priority may be increased based on the stated geographic preference. In still others, the responder may simply not be filtered out or excluded from consideration based on geographic preferences when the incident is within the stated geographic region of interest.

In some embodiments, the AED administrator/responder may be given some level of control as to how the responder network handles their geographic preferences. For example, in some embodiments, the default may be that the AED/responder will not be filtered out or excluded from consideration based on geographic preferences when an incident is within their stated geographic regions of interest. In such circumstances, although they may receive incident notification for incidents within their designated regions, they will not necessarily be notified of all incidents that occur within their designated region if other AEDs/responders are deemed more appropriate by the responder selection algorithm/mechanism. An example of a situation where this might occur is when an AED administrator has indicated that they are willing to receive notifications of incidents in a relatively large area that includes a building in which an incident is occurring (e.g., an office building, a hotel, etc.), but there are several AEDs in the building itself or much closer to the building. In such circumstances, the AED/responder selection algorithm may not choose to notify a particular AED (or responder) even if the incident is within the AEDs designated region of interest.

In some embodiments, the response profile configuration interface allows the AED administrator/responder to designate that the AED/responder should be notified of any/all incidents that occur within the designated area, regardless of whether the AED/responder selection algorithm would otherwise select that AED/responder for notification of the incident. When the AED administrator/responder has identified a region for which the AED/responder should always be notified, the AED/responder selection algorithm will cause an incident notification to be sent to the AED/responder any time an incident occurs within the designated region. Again, schools, corporate campuses and gated communities provide good examples of this use case. For example, an administrator, health officer, security guard station or other representative for any such campus may wish to always be notified of any incident occurring on the campus even if they, or the relevant AED, are not one of the closest available responders or AEDs. In such circumstances, the administrator/responder identifies the specific area/areas for which they always wish to be notified of an incident occurring within such regions. In another example, an individual may wish to be notified of any incident that occurs at their home, the home of a neighbor or loved one, their office, and/or some other specific location(s) regardless of whether they are nearby. Of course, there are many other examples of when an administrator may desire that a particular AED receive an incident notification or for which a volunteer responder may wish to receive an incident notification for any/all incidents occurring at one or more specific areas/locations.

In some implementations, the response profile configuration interface may be configured to allow the administrator/responder to separately designate both (a) an area (or areas) of interest for which they are open to receiving incident notifications; and (b) an "always notify" area (or areas) for which they would like to receive notification for any/all incidents that occur within the designated region.

In some implementations geo-fencing may additionally, or alternatively, be used in a somewhat reciprocal manner. Specifically, a responder network configuration interface can allow an administrator to designate one or more areas for which only one or more specified AEDs/responders should be notified of incidents occurring within the designated area. In such embodiments, the responder network would only notify (or select from) the specified AEDs/responders when activating a response to a potential cardiac arrest incident within the "specified response" area. Again, corporate campuses, gated communities and certain school campuses provide good examples of this use case. For example, there are many campuses, buildings, and other spaces that are not generally open or even accessible to the public. In such circumstances it may be desirable to not notify AEDs/responders that are outside of the designated region since they may not be able to enter the space anyway. In a specific example, a private building, corporate campus or a gated community may have a security guard station that has an AED and is always manned and they may prefer that any incident notification be sent to the security guard station so that the guard on-duty can respond to the incident. In some circumstances, they may also prefer that public responders outside of the area not be notified since they may not be able to enter the premises even if they appear to be right next door to an incident. Preferably, when a negative limitation of this type is requested, it will be verified by an administrator (e.g., a city or emergency services official that is responsible for a city's response network) before it is implemented to help minimize the risk that the volunteer response to an incident is not unnecessarily constrained.

Response Profile Configuration User Interface

Figure 3:
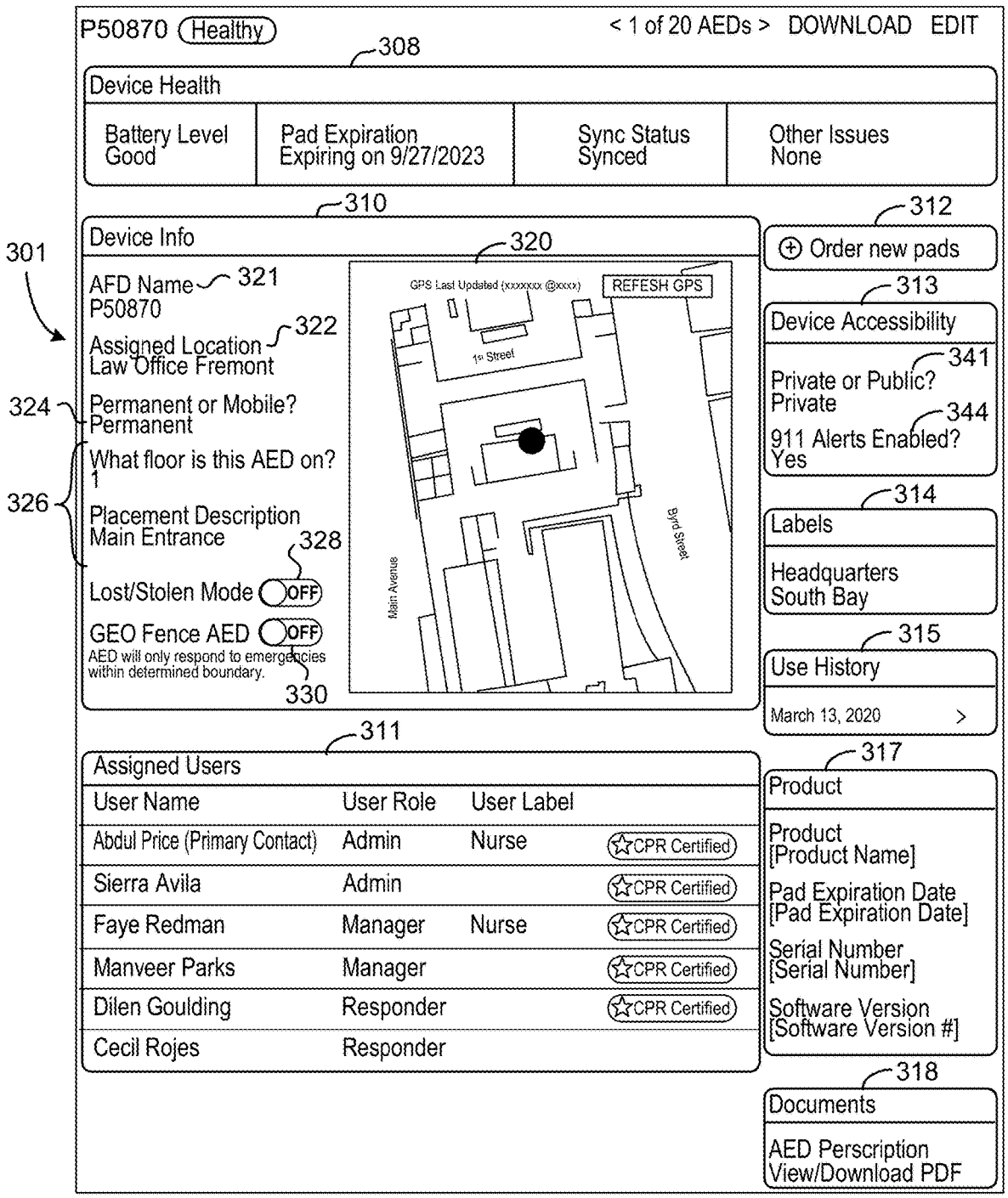
FIG. 3 is a screen shot of a computer-based user interface suitable for inputting selected responder network preferences for a medical device (e.g., an AED) in accordance with one embodiment.
Figure 4:
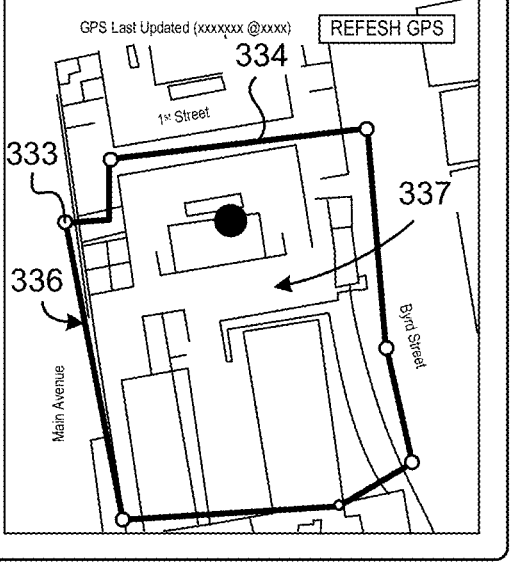
FIG. 4 is a screen shot of the user interface of FIG. 3 with a geo-fencing tool enabled to permit the user to define an area for which incident notifications are desired.

FIGS. 3-6 illustrate a few user interfaces suitable for inputting (and showing) geo-fencing and other user responder network preferences. Specifically, FIG. 3 illustrates a representative response profile configuration user interface that is incorporated into an AED management platform. The illustrated user interface takes the form of an AED management screen 301 (e.g., web page) in an AED management platform that allows a user (e.g., the AED administrator) to manage various setting. In the illustrated embodiment, the AED management screen 301 includes a Device Health box 308, a Device Info box 310, an Assigned Users box 311, an Order new pads button 312, a Device Accessibility box 313, a Labels box 314, a Use History box 315, a Product Info box 317 and a Documents box 318.

The Device Info box 310 includes several components, including a map 320 showing the AED's location, a name assigned to the AED 321, a short identification of the AED's assigned location 322, a mobility status selector 324, additional location descriptors 326, a lost/stolen mode selector 328 and Geo-Fencing selector 330. The AED name 321, location identifier 322 and location descriptors 326 each have associated text entry fields that allow the AED's administrator to enter appropriate information into the record.

The mobility status selector 324 allows the administrator to designate the AED as either a stationary ("permanent") AED or as a mobile AED. In general, permanent AEDs are expected to be kept at a fixed location, whereas mobile AEDs are expected to be moved around (e.g., an AED that will be kept in a vehicle or carried around by its user). It should be appreciated that the AED responder network server 20 may optionally treat the AED somewhat different based on whether AED is designated as a permanent or mobile AED. For example, in some implementations, the AED selection algorithm may directly send a nearby incident notifications to a permanent AED that is known to be close to an incident location without first verifying its location, whereas the present location of a mobile AED may be determined or verified before it is notified of an incident to better identify mobile AEDs that are nearby an incident and to reduce the probability of an AED being notified of an incident for which it can't practically be used for because it is too far away. In another example, an AED map that shows the location of AEDs may be configured to only show permanent AEDs since there is a higher risk that mobile AEDs may not be available if someone goes to try to retrieve it. In other implementations, a mobile AED may be shown on the AED map only after its current location has been verified. In yet another example, the responder network's AED selection algorithm may apply different selection criteria to mobile AEDs—and particularly to AEDs thought to be in vehicles since a vehicle may be able to be timely brought to an incident that is further from the AED than a fixed location AED. For example, the selection algorithm may check-in with mobile AEDs that were last known to be within a wider radius than stationary AEDs since they are more likely to have moved since their last check-in and may therefore be available to respond to a nearby incident.

When the lost/stolen indicator 328 is set to "on", the AED management server can institute a lost AED location identification protocol in an effort to determine the current location of the AED and, if found, notify the AED's administrator of the AED's current location.

The Geo-Fencing selector 330 provides a mechanism by which the AED's administrator may set boundaries that define an area for which the AED may be notified of nearby incidents as previously discussed. In some embodiments, when geo-fencing is turned "on" the user is able to "draw" the desired notification area on the map. There are a number of conventional mapping/drawing techniques that can be used to define the desired notification area. By way of example, in the embodiment illustrated in FIG. 4, the user simply inputs selected boundary points 333 and a mapping algorithm draw boundary 334 lines between the boundary points to create a bounding box 336 that defines the desired notification area 337. The shape of the bounding box 336 may readily be altered by adding boundary points 333, dragging existing boundary points to new location etc. as will be readily appreciated by those familiar with such mapping technologies. The responder network's AED selection algorithm can then use the defined notification area 337 in its selection of AEDs to be notified in the event that an incident occurs in the general vicinity of the specific AED. Although a particular geo-fencing implementation is shown, it should be appreciated that the desired notification area can be defined in a wide variety of different manners utilizing a variety of different interfaces. For example, the restricted area can be defined by an address, a set of addresses, postal codes, geo-coordinates (e.g., GPS or other GNSS coordinates), street boundaries, a free-form drawing tool or any other suitable mechanism now existing or later developed.

The Device Accessibility Box 313 also contains information/user preferences that are relevant to the responder network. In the illustrated embodiment, the Device Accessibility Box 313 includes a Public/Private selector 341 and a 911 Alerts enablement selector 344. The Public/Private selector gives the administrator a mechanism for indicating whether the AED is a public access AED (e.g., members of the public are free to come get that AED if there is a nearby cardiac areres incident) or, a private AED, which members of the public are generally not encouraged to try to locate. Public and private AEDs may be handled somewhat differently by the responder network. For example, in some implementations, public access AEDs may appear on public access AED maps that show the location(s) of AEDs, whereas the location of private AED may not be shown on such maps, or shown differently on the maps to indicate their "private" status. It should be appreciated that the owner(s) of AEDs that are located in restricted areas (e.g., a locked building, a home, etc.) may not want the general public to try to access an AED located in such locations.

In another example, in the context of a volunteer responder network, both public and private AEDs may receive notifications of nearby incidents from the responder network, but a member of the public would not be directed to, or shown the location of, a private AED in the event of an incident since it may not be publicly available. Reaching further, when a responder network in integrated with emergency services answering services (PSAPs) a computer aided dispatch (CAD) system or other interface available to a PSAP dispatcher may be configured to display a map of the area around an incident that shows the location of public access AEDs. AEDs marked "private" may not be shown to the dispatcher in such systems unless or until they have accepted a nearby incident (e.g., a volunteer responder has indicated a willingness to bring the AED to the site of a nearby potential cardiac arrest incident). By way of example, some such systems are described in U.S. Patent Application No. 63/242,610 (P025P), which is incorporated herein by reference.

Preferably, participation in the volunteer responder network is an opt-in system. Thus, when the response profile configuration interface is part of an AED management interface, it may include a GUI widget that facilitates opting into notifications. In the embodiment of FIG. 3, this takes the form of 911 Alerts enablement selector 344 (labeled "911 Alerts enabled?"), which allows the AED administrator to enable or disable nearby incident alerts to the associated AED. As such, the 911 Alerts enablement selector allows the AEDs administrator to "opt-in" to nearby incident notifications or to disable this feature, as desired. If 911 alerts are not enabled, the responder network will not send nearby incident notifications to the associated AED even if the AED is nearby a potential cardiac arrest incident.

It should be appreciated that the Public/Private selector 341 and the 911 Alerts enablement selector 344 serve quite different functions. As such, nearby incident notifications may be sent to both public and private AEDs in accordance with their owner/administrator's preferences. Similarly, AEDs may be designated as "public" AEDs such that they show up on relevant AED maps, regardless of whether their owner/administrator has opted into 911 notifications.

In some embodiments the management platform user interface (e.g., the AED management screen 301) may optionally include a "Notify 911" (notify emergency services) selector (not shown). When the Notify 911 selector is turned on, the associated AED is configured to automatically notify emergency services that an AED has been activated for use and provide its current location. In this context, the notification may be sent to the PSAP that is responsible for the AEDs then current location any time that the AED is activated. Such notifications can take the form of an AED Activated message sent directly or indirectly from the AED to the responsible PSAP. Such notifications that there is an active AED at a particular location can serve multiple purposes. For example, if a bystander calls 911 from a generally similar location it can inform the dispatcher that there is an AED on the scene and provide additional confirmation of the location of the incident. In other circumstances, the AED Activated message can serve as the initial notification of an emergency incident that is received by the PSAP and the incident can thereafter be handled in accordance with such PSAPs preferred response protocols. When a Notify 911 selector is provided, it gives the AED's owner/administrator the ability to either activate, or turn off this feature. Such selectors can be provided as part of a response profile user interface for a particular AED (such as the UI illustrated in FIGS. 3 and 4), or as part of a user interface that facilitating applying user preference settings to a group of AEDs (such as the UI illustrated in FIGS. 5 and 6).

In other embodiments, the Notify 911 selector can be used to facilitate other emergency services communications schemes. For example, the AED can be configured to automatically initiate a voice call to emergency services (e.g., 911) when the Notify 911 selector is activated, or to initiate a two-way voice and/or data communication channel between the AED and a PSAP operator when the Notify 911 selector is activated.

Communications between the AED 10 and the PSAP 25 can be facilitated in a variety of ways. In some circumstances a direct communications link can be made between the AED and the relevant PSAP. However, in other embodiments, the communications may be made via the AED network server 20 and/or the emergency services interface 28. As discussed in many of the incorporated patent applications including U.S. Patent Application No. 63/242,610 (P025P), it is believed that there are significant implementation and security advantages to utilizing a suitable intermediary such as an AED network server, an emergency services interface and/or other suitable intermediary server(s) to facilitate communications between the AED 10 and the PSAP 25.

Figure 5:
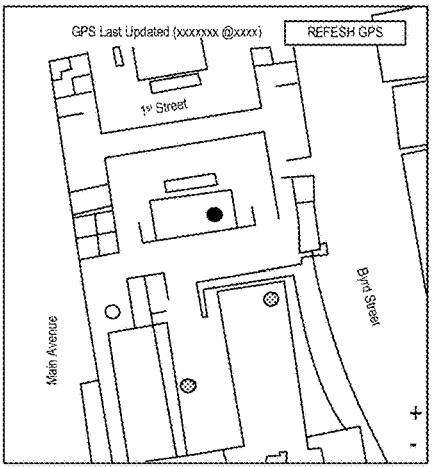
FIG. 5 is a screen shot of a computer-based user interface suitable for inputting selected responder network preferences in accordance with another embodiment.

Turning next to FIGS. 5 and 6, an interface suitable for inputting location availability type geofencing will be described. FIG. 5 is a screen-shot illustrating a user interface that is particularly useful for entities that may be responsible for managing multiple AEDs and/or the entity's response to potential cardiac arrest incidents. In the illustrated embodiment, a Location Management screen 360 includes a Location Status box 363, an AED Assignments box 365, a Location information box 366, a Location Accessibility box 368, a Locations Label box 371, a Store box 373, a User Assignments box 375 and a Documents box 376. The AED Assignments box 365 and the Location Accessibility box 368 are the two features that are most relevant to the present disclosure. The Location Accessibility box 368 includes Public/Private selector 378 and Location Geo-fencing selector 380. The Public/Private selector 378 is much like the Public/Private selector 341 discussed above, with the primary difference being that Public/Private selector 341 in FIG. 3 sets the Public/Private status only for the associated AED, whereas the Public/Private selector 378 allows the administrator to set the Public/Private status for a set of AEDs that are managed by the administrator—which could be a single AED, a few AEDs or hundreds or thousands of AEDs depending on the circumstances. In the illustrated circumstances, the AEDs are designated as "Public" AEDs. Thus, an Availability indicator 379 is rendered that indicates the times that the AEDs are publicly available. This is particularly important in circumstances in which an AED is located inside a business, building or other space that is open (and thus accessible) only part of the date. It is noted that the Availability indicator is rendered because the AEDs have been identified as Public AEDs and therefore the hours at which the AED is available to the public is pertinent. A similar Availability indicator would be rendered in Device Accessibility box 313 on AED management screen 301 of FIG. 3 if the associated AED had been marked as "Public."

The Location Geo-Fencing selector 380 provides a mechanism by which the location manager can designate an area for which only selected AEDs will be notified of an incident. As discussed above, this feature can be particularly useful in restricted campus/building/spaces where it might not be desired, practical, or even possible for outsiders to enter the premise where an incident is occurring. In some embodiments, the default is to have the location geo-fencing off—and this state is shown in FIG. 5. However, when geo-fencing is turned on, a mechanism is provided to permit the administrator to define the restricted area. For example, in the embodiment illustrated in FIG. 6, a tool (e.g., a drawing or mapping tool) is enabled to permit the administrator to enter the boundaries of the restricted area. The drawing/mapping tool may be similar to the tool described above with respect to FIG. 4 or take any other suitable form. However, the designated area is treated differently—e.g., only AEDs and/or responders that are within the designated area and/or are designated by the administrator will be notified of incidents occurring within the designated area. In the illustrated embodiment, the restricted area 397 may be defined graphically by a user by inserting boundary points 393. A mapping algorithm then inserts boundary lines 394 between the boundary points 393 to define a bounding box 396 that defines the desired restricted area 397. Although a particular geo-fencing implementation is shown, it should be appreciated that the restricted area can be defined in a wide variety of different manners utilizing a variety of different interfaces as previously discussed.

Responder Network Integration and Responder Selection Algorithm

When the administrator/responder has entered responder network preferences, those preferences are conveyed to the responder network server where they can be stored in a responder database. The selection algorithm that identifies AEDs and/or responders to notify of a nearby incident then utilizes the stated preferences when it determines what/which AEDs and/or responders to notify of a nearby incident.

When the responder network receives a request to activate the responder network, it typically receives an indication of the location of the incident. This makes it practical to implement the geo-fencing type of responder preferences discussed above. By way of example, FIG. 7 is a flow chart that illustrates one suitable approach for implementing geo-fencing type responder preferences.

Figure 7:
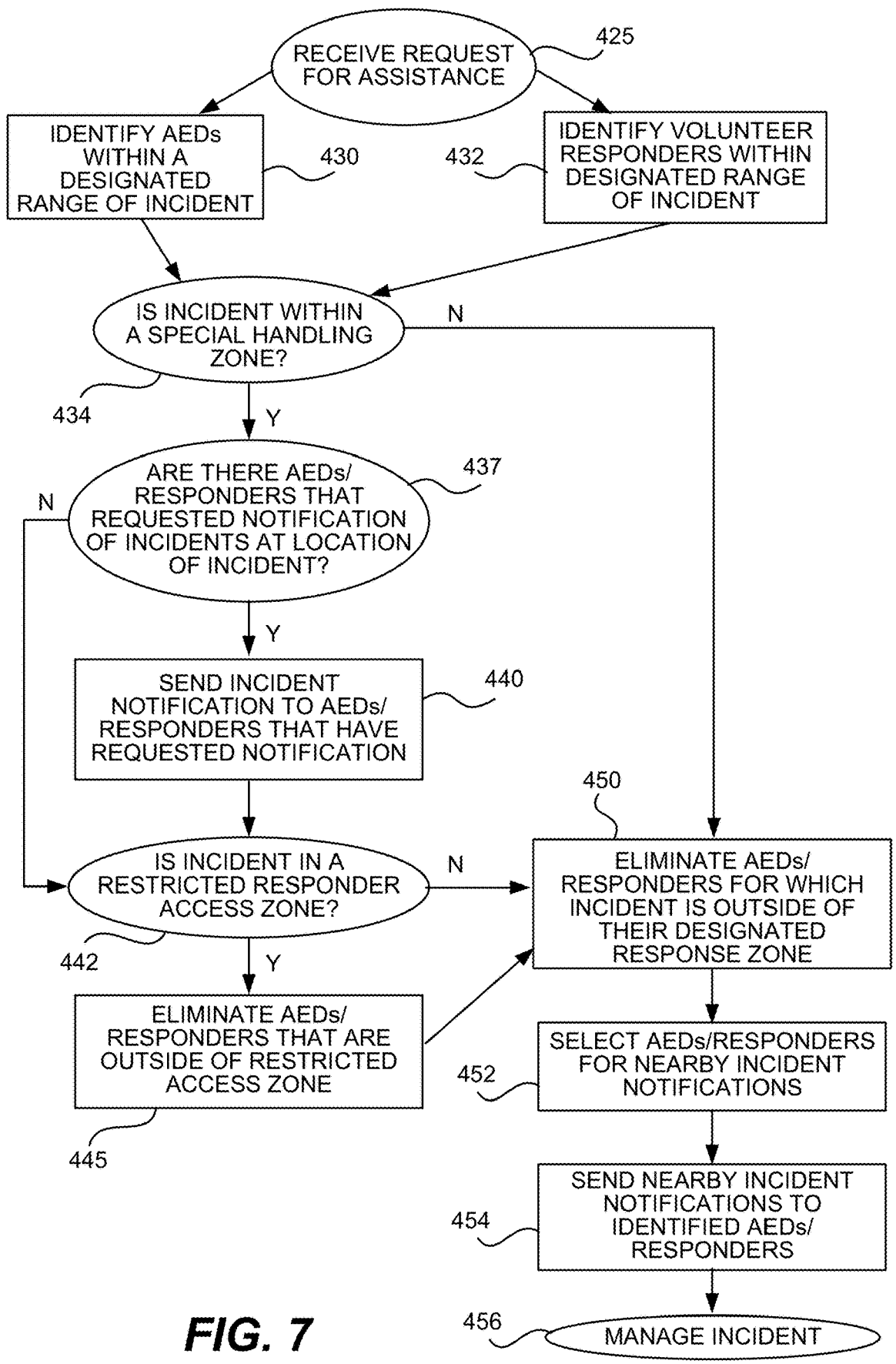
FIG. 7 is a flow chart illustrating one approach for identifying medical devices to notify of a nearby incident.

In the embodiment of FIG. 7, the process begins when the AED responder network server 20 receives a request for volunteer assistance in responding to a potential cardiac arrest incident. Block 425. The server identifies AEDs (block 430) and volunteer responders (block 432) that are within a designated range of the incident. As previously discussed, the ranges for these initial filtering may vary widely based on system design choices and the thresholds used do not need to be the same for the AEDs and the volunteer responders. In some embodiments, this initial filtering may be based response time estimates or other factors if desired. As discussed in some of the incorporated patents, in some situations the initial range is quite expansive and some, or all of the AEDs and/or volunteer responders may be pinged to verify their current location.

The AED network server also determines whether the incident is within a special handling zone as represented by block 434. In this context, special handling zones include restricted access zones and/or areas for which a responder/AED has requested that the responder network always notify them of incidents occurring therein. If there are any AEDs and/or volunteer responders and/or stations that have requested that they always be notified of incidents occurring at the location of the incident (as represented by decision block 437), those devices/responders are sent incident notifications as represented by block 440.

Furthermore, if the incident is in a recognized restricted access zone (as represented by decision block 442), the responder selection algorithm eliminates any device/responders that are outside of the restricted access zone from consideration for inclusion in the potential responder pool as represented by block 445.

Regardless of whether the incident requires special handling, the responder selection algorithm also eliminates any AEDs/responders for which the incident lies outside of their designated response zone as represented by block 450.

The user geographic preference-based filtering of responder candidates is relatively easy to implement because the responder network typically receives the location of the incident with the request to activate the responder network. The location information may include GPS coordinates, a street address, and/or other suitable location identifying information. Such location information can readily be compared with the geographic constraints for candidate responders that are known or determined by the responder network to be in the general region of the incident.

Although not explicitly shown in the flow chart of FIG. 7, if/when other user preferences are supported, the responder selection algorithm would eliminate any devices/responders for which the incident fell outside of the responder defined preferences. The responder selection algorithm would then select a set of AEDs/responders to notify of the incident from the pool of remaining incidents/devices as represented by block 452. As discussed above, a wide variety of different selection algorithms and/or Nearby incident notifications are then sent to the selected AEDs/responders as represented by block 454. Thereafter the incident is managed in accordance with the appropriate responder network protocols. In some circumstances emergency services (e.g., a PSAP operator/dispatcher) may be involved in the management of the incidents. By way of example, U.S. Patent Application No. 63/242,610, which is incorporated herein describes a framework for supporting such PSAP/public responder network integrations.

It should be appreciated that in some circumstance where there may be a set of one or more AEDs/responders/stations that are always to be notified of an incident in a particular area (e.g., in an assisted living community or a closed campus) and there may be no need or desire to send notifications to any devices/responders outside of the set of devices to always be notified of an incident for that area. If desired a restricted access zone can be set up such that an exclusive defined set of one or more devices/stations/responders is always notified of an incident and by rule, no other devices or responders are notified of the incident. When desired, the user interface associated with defining restricted access zones can readily be configured to support the definition of such exclusive lists.

In the description above (including, but not limited to, the descriptions of the flow charts of FIGS. 2 and 7), a number of steps have been described and/or are illustrated in a particular order to facilitate an explanation of the invention. It should be appreciated that except where the context requires a specific order, the relative timing of the various steps and/or the order in which these steps occur may vary and/or various steps may be combined, and/or added and/or deleted. For example, as will be appreciated by those familiar with modern selection algorithms, a single instruction can be often used to filter a dataset based on multiple/many different parameters such that many of the described filtering steps may effectively be performed concurrently.

As described in some of the incorporated patents, the responder network server may be designed to ping some, or all AEDs and volunteer responders that are suspected or expected to be within some distance of the incident to (a) get their current location, (b) verify that they are able to communicate and (c) for AEDs, verify that they are currently in good operating condition. This initial request is not an incident notification and is typically done without any visibility by the potential responder. In some embodiments, the devices that respond to this status inquiry are considered responder candidates. In some implementations, any geographic constraints associated with the responder candidates may be considered at this time. In parallel, or alternately, there may be some or many responders/AEDs that the responder network does not need to ping prior to considering such responders/devices to be candidate responders. Regardless of the way that responder candidates are identified, the responder selection algorithm selects an appropriate set of responders to be notified of the incident from the set of candidate responders.

As described in some of the incorporated patents, there are a number of ways that potential responders may be notified of a potential incident. For example, incident notifications may be sent directly to an AED, to a cell phone or other mobile communication device associated with a responder, via virtual assistant or in any other suitable manner. The described geo-fencing may be applied regardless of the manner in which a responder elects to receive incident notifications.

The description above focuses primarily on geographic based user preferences. However, it should be appreciated that the responder selection algorithm may be configured to consider other user preferences as well. For example, if the responder network addresses different types of incidents—e.g., cardiac arrest, opioid overdoses, snake bites (or other poisonous bites), etc., the responder may select the type of incidents that they are willing to respond to. In such implementations the set of medical devices that are available for notification may include devices such as first aid kits, anti-venom kits, epinephrine injectors (often used to on patient's suffering from severe allergic reactions (anaphylaxis)), Naloxone nasal spray devices (often used to treat opioid overdoses), stop-the-bleed kits, medical supply kits, etc.

Similarly, although the description focuses primarily on public responder networks tailored to generating a volunteer responder response to sudden cardiac arrest incidents, the same principles are readily applied to other types of responder networks including venomous bite, overdose, allergic reaction or other types of volunteer responder networks, and particularly those that incorporate notifying devices of the incident.

Although only a few embodiments of the invention have been described in detail, it should be appreciated that the invention may be implemented in many other forms without departing from the spirit or scope of the invention. For example, although only a few of the selection criteria have been described in detail, it should be apparent that the responder selection algorithm can consider a wide variety of factors when determining which devices and/or responders to notify of any particular incident.

In most of the description above, the responder network is described as sending nearby incident notifications to volunteer responders and/or medical devices such as AEDs. It should be appreciated that there are a wide variety of different devices to which nearby incident notifications can be sent. For example, many homes now have virtual assistants and nearby incidents messages can be sent to such systems. Examples of such a system is described in U.S. Provisional Patent Application No. 62/938,456 which is incorporated herein by reference. Some neighborhoods also have local responder networks. Notifications can be sent from the responder network server (20) to such systems for distribution to their respective members, or servers in such systems may serve as the responder network server.

Further, it should be appreciated that incident notification that are sent to a medical device can be sent to the medical device itself, or a module that is associated with the medical device. For example, if a cabinet or case that houses a medical device (e.g., an AED) has communication capabilities incident notifications can be sent to the cabinet/case. In such circumstances, the nearby incident alerts can be generated by the cabinet/case itself, the medical device housed therein, or any other associated component. In another example, as described above, some defibrillators/AEDs may be modular defibrillator systems that include an interface unit that is mounted on and detachably attached to a base defibrillator unit to provide unitary portable modular defibrillator system. In such implementations, the incident notifications can be sent to the interface unit and the nearby incident alerts can be generated by either the base defibrillator unit or the interface unit. Similarly, communications initiated by the defibrillator in such systems can technically be initiated by either the base defibrillator unit or the interface unit. Therefore, the present embodiments should be considered illustrative and not restrictive, and the invention is not to be limited to the details given herein, but may be modified within the scope and equivalents of the appended claims.

What is claimed is:

1. A method of managing incident notifications in a public responder network the method comprising:
    for at least a first defibrillator that is included in the public responder network, receiving an administrator or user settable defibrillator preference;
    in response to the reception of a request to activate the public responder network, executing a selection algorithm to identify a set of one or more selected defibrillators that are included in the public responder network to be notified of a potential cardiac arrest incident, wherein a determination of whether to include the first defibrillator in the set of selected defibrillators is based at least in part on the received administrator or user settable defibrillator preference; and
    sending a nearby incident notification to each of the selected defibrillators, wherein each selected defibrillator is configured to generate a nearby incident alert in response to the reception of the corresponding nearby incident notifications to encourage individuals that perceive the nearby incident alert to take such selected defibrillator to the potential cardiac arrest incident.

2. A method as recited in claim 1 wherein the administrator or user settable defibrillator preference is or includes a selected mobility setting associated with the first defibrillator.

3. A method as recited in claim 1 wherein the selected mobility setting is selected from a set of available mobility settings that include:
    a stationary setting that indicates that the first defibrillator is expected to be kept at a fixed location; and
    a mobile setting that indicates that the first defibrillator is expected to be moved around.

4. A method as recited in claim 1 wherein the administrator or user settable defibrillator preference is or includes a selected device accessibility setting associated with the first defibrillator.

5. A method as recited in claim 4 wherein the selected public accessibility setting is selected from a set of available device accessibility settings that include:
    a public setting that indicates that the first defibrillator is available to the public; and
    a private setting that indicates that the first defibrillator is not available to the public.

6. A method as recited in claim 1 wherein the administrator or user settable defibrillator preference is or includes a selected incident notifications setting associated with the first defibrillator.

7. A method as recited in claim 6 wherein the selected incident notifications setting is selected from a set of available device accessibility settings that include:
    an incident notifications enabled setting that indicates that notifications of nearby potential cardiac arrest incidents are authorized to be sent to the first defibrillator; and
    an incident notifications not enabled setting that indicates that notifications of nearby potential cardiac arrest incidents are not authorized to be sent to the first defibrillator.

8. A method as recited in claim 1 wherein the administrator or user settable defibrillator preference is selected from a set of available device accessibility settings that include:
    an always notify option, wherein when the always notify option is selected, the selection algorithm will cause the first defibrillator to be included in the set of selected defibrillators any time a request to activate the public responder network is received for a potential cardiac arrest incident occurring within a designated area associated with the first defibrillator; and
    an available option, wherein when the available option is selected and an incident occurs within the designated area, the selection algorithm may optionally include the first defibrillator in the set of selected defibrillators based on other factors.

9. A method as recited in claim 1 wherein the first defibrillator is an automated external defibrillator (AED).

10. A method as recited in claim 9 wherein the AED is a modular defibrillator system that includes a fully functional base defibrillator unit and an interface unit that is mounted on and removably attached to the base defibrillator unit to provide a unitary modular defibrillator.

11. A responder network server configured to manage incident notifications in a defibrillator inclusive volunteer responder network, wherein each defibrillator in the volunteer responder network is configured to generate a nearby incident alert in response to the reception of a nearby incident notifications to encourage individuals that perceive the nearby incident alert to take such defibrillator to a potential cardiac arrest incident, the responder network server being configured to:

for at least a first defibrillator that is included in the volunteer responder network, receive a first administrator or user settable defibrillator preference;

in response to the reception of a request to activate the volunteer responder network, execute a selection algorithm to identify a set of one or more responder targets to be notified of a first potential cardiac arrest incident, wherein a determination of whether to include the first defibrillator in the set of responder targets is based at least in part on the received first administrator or user settable defibrillator preference; and send first nearby incident notifications to the identified set of responder targets, whereby each defibrillator that receives one of the first nearby incident notifications generates a corresponding first nearby incident alert to encourage individuals that perceive the first nearby incident alert to take such defibrillator to the first potential cardiac arrest incident.

12. A responder network server as recited in claim 11 wherein the first administrator or user settable defibrillator preference is or includes a selected mobility setting associated with the first defibrillator.

13. A responder network server as recited in claim 11 wherein the selected mobility setting is selected from a set of available mobility settings that include:
a stationary setting that indicates that the first defibrillator is expected to be kept at a fixed location; and
a mobile setting that indicates that the first defibrillator is expected to be moved around.

14. A responder network server as recited in claim 11 wherein the first administrator or user settable defibrillator preference is or includes a selected device accessibility setting associated with the first defibrillator.

15. A responder network server as recited in claim 14 wherein the selected public accessibility setting is selected from a set of available device accessibility settings that include:
a public setting that indicates that the first defibrillator is available to the public; and
a private setting that indicates that the first defibrillator is not available to the public.

16. A responder network server as recited in claim 11 wherein the first administrator or user settable defibrillator preference is or includes a selected incident notifications setting associated with the first defibrillator.

17. A responder network server as recited in claim 16 wherein the selected incident notifications setting is selected from a set of available device accessibility settings that include:
an incident notifications enabled setting that indicates that notifications of nearby potential cardiac arrest incidents are authorized to be sent to the first defibrillator; and
an incident notifications not enabled setting that indicates that notifications of nearby potential cardiac arrest incidents are not authorized to be sent to the first defibrillator.

18. A responder network server as recited in claim 11 wherein the first administrator or user settable defibrillator preference is selected from a set of available device accessibility settings that include:
an always notify option, wherein when the always notify option is selected, the selection algorithm will cause the first defibrillator to be included in the set of selected defibrillators any time a request to activate the public responder network is received for a potential cardiac arrest incident occurring within a designated area associated with the first defibrillator; and
an available option, wherein when the available option is selected and an incident occurs within the designated area, the selection algorithm may optionally include the first defibrillator in the set of selected defibrillators based on other factors.

19. A responder network server as recited in claim 11 further configured to:
for at least a second defibrillator that is included in the volunteer responder network, receiving a second administrator or user settable defibrillator preference indicative of at least one of (i) an indication of a mobility status of the second defibrillator, (ii) an indication of a public accessibility of the second defibrillator, and (iii) an indication of whether incident notifications are permitted for the second defibrillator; and
wherein the set of responder targets selected for the first potential cardiac arrest incident is further based on at in part on the received second administrator or user settable defibrillator preference.

20. A responder network server as recited in claim 11 wherein the first defibrillator is an automated external defibrillator (AED).

21. A non-transitory computer readable medium embodying programmed instructions configured to cause the display of a graphical user interface for setting user preferences associated with a first defibrillator's participation in a defibrillator inclusive volunteer responder network, wherein each defibrillator in the volunteer responder network is configured to generate a nearby incident alert in response to the reception of a nearby incident notification to encourage individuals that perceive the nearby incident alert to take such defibrillator to a potential cardiac arrest incident, the display of a graphical user interface comprising at least one of:
(i) a mobility status selector for designating a mobility status of the first defibrillator;
(ii) a public accessibility selector for designating a public accessibility of the first defibrillator;
(iii) an incident notifications selector for designating whether nearby incident alerts are permitted for the first defibrillator; and
(iv) a geographic preference selection mechanism for designating a geographic preference associated with the first defibrillator.

* * * * *